(12) United States Patent
Bingabr

(10) Patent No.: US 11,103,702 B2
(45) Date of Patent: Aug. 31, 2021

(54) METHOD AND SYSTEM TO STIMULATE THE INTRACOCHLEAR ELECTRODES IN COCHLEAR IMPLANTS

(71) Applicant: UNIVERSITY OF CENTRAL OKLAHOMA, Edmond, OK (US)

(72) Inventor: Mohamed G. Bingabr, Edmond, OK (US)

(73) Assignee: University of Central Oklahoma, Edmond, OK (US)

(*) Notice: Subject to any disclaimer, the term of this patent is extended or adjusted under 35 U.S.C. 154(b) by 368 days.

(21) Appl. No.: 16/112,087

(22) Filed: Aug. 24, 2018

(65) Prior Publication Data

US 2019/0060650 A1    Feb. 28, 2019

Related U.S. Application Data

(60) Provisional application No. 62/549,781, filed on Aug. 24, 2017.

(51) Int. Cl.
*A61N 1/36* (2006.01)
*A61N 1/05* (2006.01)

(52) U.S. Cl.
CPC ........ *A61N 1/36038* (2017.08); *A61N 1/0541* (2013.01)

(58) Field of Classification Search
CPC .......................... A61N 1/36038; A61N 1/0541
See application file for complete search history.

(56) References Cited

U.S. PATENT DOCUMENTS

2004/0136556 A1\* 7/2004 Litvak ............... A61N 1/36038
381/316

OTHER PUBLICATIONS

Buchner, A., Frohne-Buechner, C., Gaertner, L., Lesinski-Schiedat, A., Battmer, R., and Lenarz, T., "Evaluation of advanced bionics high resolution mode", International Journal of Audiology, vol. 45, No. 7, pp. 407-416, 2006.
Cochlear, "ACE and CIS DSP Strategies: Software Requirements Specification", Part No. N95287F Issue 1 Oct. 2002.
(Continued)

*Primary Examiner* — Mallika D Fairchild
(74) *Attorney, Agent, or Firm* — Berenato & White, LLC

(57) ABSTRACT

The present invention provides a method implementing a speech strategy based on zero crossing behavior of speech time waveforms; the zero crossing containing both spectral and temporal speech information. This method uses temporal information of speech to activate electrodes instead of spectral information; maps temporal segment durations to spatial durations along the basilar membrane inside the cochlea; and provides instantaneous, continuous information about speech to electrodes that stimulate the auditory nerve. Timing of oval window mechanical motion is represented by zero crossings which are used to activate electrodes implanted inside the cochlea. Motion of the tympanic membrane, and the oval and round windows, follow the speech signal temporal waveform. Positive segments of the temporal waveform cause inward displacement of the oval membrane from its stationary position and negative segments causes outward retraction of the membranes. Temporal waveform zero-crossings indicate time instants when the membranes are in their stationary positions.

4 Claims, 6 Drawing Sheets

(56) References Cited

OTHER PUBLICATIONS

Greenberg, S., "Understanding speech understanding: Towards a unified theory of speech perception., Proceedings of the ESCA Workshop on the Auditory Basis of Speech Perception," Keele University, 1996, pp. 1-8.

Kemp, "Otoacoustic emissions, their origin in cochlear function, and use", British Medical Bulletin 2002;63: 223-241.

Loizou, P., "Mimicking the Human Ear: An Overview of Signal-Processing Strategies for Converting Sound into Electrical Signals in Cochlear Implants.", IEEE Signal Processing Magazine Sep. :101-130, 1998.

Moore, B., and Peters, R., "Pitch discrimination and phase sensitivity in young and elderly subjects and its relationship to frequency selectivity", J. Acoust. Soc. Am. 91 (5), May 1992.

Nie, K., Barco, A., and Zeng, FG., "Spectral and Temporal Cues in Cochlear Implant Speech Perception.", Ear & Hearing, vol. 27, No. 2, 208-217, 2006.

O'Leary et al., "Current distributions in the cat cochlea: A modelling and electrophysiological study", Hearing Research, 18 (1985) 273-281.

Paliwal, K., and Alsteris, L., "Usefulness of phase spectrum in human speech perception", in Proc. Eur. Conf. Speech Communication and Technology (Eurospeech), Geneva, Switzerland, pp. 2117-2120, Sep. 2003.

Raphael, Y., Altschuler, R., "Structure and innervations of the cochlea", Brain Research Bulletin 60: pp. 397-422, 2003.

Rebscher et al., "Considerations for design of future cochlear implant electrode arrays: Electrode array stiffness, size, and depth of insertion", JRRD, vol. 45, pp. 731-748; No. 5, 2008.

Rebscher SJ, et al., "Design and fabrication of multichannel cochlear implants for animal research", J Neurosci Methods (2007), doi:10.1016/j.jneumeth.2007.05.013.

Robles et al., "Mechanics of the Mammalian Cochlea", The American Physiological Society, Physiological Reviews, vol. 81, No. 3, pp. 1305-1352; Jul. 2001.

Shamma et al., "On the balance of envelope and temporal fine structure in the encoding of speech in the early auditory system", J. Acoust. Soc. Am. 133 (5), pp. 2818-2833, May 2013.

Shannon, R., Fu, Q., and Galvin III, J., "The number of spectral channels required for speech recognition depends on the difficulty of the listening situation.", Acta Otolaryngol, suppl 552:50-54, 2004.

Shi, G., Shanechi, M., and Aarabi, P., "On the Importance of Phase in Human Speech Recognition.", IEEE transactions on audio, speech, and language processing, vol. 14, No. 5, Sep. 2006.

Snyder et al., "Cochlear Implant Electrode Configuration Effects on Activation Threshold and Tonotopic Selectivity", Hear Res. Jan. 2008 ; 235(1-2): 23-38.

Wilson et al., "Cochlear implants: Current designs and future possibilities", JRRD, vol. 45, pp. 695-730, No. 5, 2008.

Wiltbrodt et al., "Developing a Physical Model of the Human Cochlea Using Microfabrication Methods", Audiol Neurotol 2006;11:104-112, DOI: 10.1159/000090683.

Zatorre R., and Belin, P., "Spectral and Temporal Processing in Human Auditory Cortex", Cerebral Cortex Oct. 2001; vol. 11: 946-953.

\* cited by examiner

METHOD AND SYSTEM TO STIMULATE THE INTRACOCHLEAR ELECTRODES IN COCHLEAR IMPLANTS

CROSS REFERENCES TO RELATED APPLICATIONS

This application claims the benefit of U.S. Provisional Patent Application No. 62/549,781 filed on Aug. 24, 2017 in the name of Mohamed B. Bingabr, which is expressly incorporated herein by reference in its entirety.

FIELD OF THE INVENTION

The present invention generally relates to communication (Auditory) strategies for the hearing impaired. More particularly, the present invention is directed to cochlear implants (CI) to stimulate the auditory nerve fibers in the cochlea to restore the hearing sensation in people with severe or profound hearing loss.

BACKGROUND OF THE INVENTION

There are two main components to a cochlear implant system. The internal component is the implant. The external component is a sound processor, which can be worn on or off the ear. Cochlear implants (CI) use electrodes to stimulate the auditory nerve fibers in the cochlea to restore hearing sensation in people with severe or profound hearing loss. However, cochlear implant users show a wide range performance variability, even with the same hearing history and use of the same technology. Contemporary cochlear-implant Speech Coding Strategies (SCS) are based on coding the spectral bands of the speech to activate intracochlear electrodes. The mapping of the spectral bands to the intracochlear electrodes is based on the "place principle" which depends on the tonotopic theory of the basilar membrane described by Nobel Prize laureate Georg von Bekesy (Place Theory of Hearing). The basilar membrane vibrates at the base for high frequencies and, as the frequency decreases, the vibration location moves toward the apex. Low frequency spectral bands will activate electrodes at the apex, and high frequency spectral bands will activate electrodes at the base.

"Place" and the "temporal" coding are the two hypotheses that explain the ability to discriminate sounds of different frequencies. Tones of different frequencies will cause the basilar membrane to vibrate with higher amplitudes at different locations along the basilar membrane. The basilar membrane vibrates near the base for high frequency and near the apex for low frequency. The temporal principle is based on the firing rate of the auditory nerve fibers. Neurons firing rate is in synchrony with the frequency of the stimulus up to 1200 Hz. Contemporary SCSs for cochlear implants are based on the place principle mapping of the spectral bands to the intracochlear electrodes.

The place principle holds true for tone experiments, but for complex tones (tone with multiple frequencies) it has been shown that the basilar membrane does not vibrate according to the place principle. Also, the basilar membrane is not a linear system, so its response to two separate tones will not be the same as the response to the two tones added together. Scientifically and experimentally it has been shown that the motion of the oval window, which disturbs the fluid inside the cochlea and the basilar membrane, follows the temporal waveform in the speech. The oval window is one of the two openings from the middle ear into the inner ear (see FIG. 1). It is sealed by the secondary tympanic membrane (round window membrane), which vibrates with opposite phase to vibrations entering the inner ear through the oval window. Speech is a complex signal with thousands of frequencies. It is difficult to measure the motion of the basilar membrane at different locations without destroying the physical characteristics of the cochlea so no one knows how it vibrates for complex speech signals. The motion of the basilar membrane may also be a spatial map of the temporal waveform that stimulates the auditory nerves.

Contemporary speech strategy defines a process that takes segments of the speech with durations that range from 10 to 25 milliseconds, performs a fast Fourier transform on the segment, then identifies the spectrum bands with the highest power, delivering current pulses to electrodes that are proportional to the power of the spectral bands. Present methods depend on the spectral information to activate electrodes inside the cochlea. The spectral bands determine the location of the activated electrodes, such as high frequency spectral band to electrode in the base and low frequency spectral band to electrode near the apex of the cochlea. (see FIG. 2). A microphone will pick up an acoustic speech signal and convert it to an electrical signal. The electrical signal will pass through 4 to 16 band-pass filters with different cutoff frequencies. For example, as shown in FIG. 2 the first bandpass filter low and high cutoff frequencies are 20 and 1000 Hz, respectively. The output of the bandpass filter is passed through an envelop detector to extract the envelop of the bandlimited temporal waveform. The envelop of the waveform will modulate the amplitude of the bipolar electric pulse that will be transmitted to the corresponding electrode. In the actual speech processor, the filtering is done by a chip that calculates the fast Fourier Transform (FFT), then the strongest (in terms of energy) 4 to 16 bands are selected to activate the electrodes. Different systems presently available implement speech strategies that use the spectral band to activate the electrode, but have some variation on the number of electrodes used, channels bandwidth, and pulse rate, electrode configuration, and the mechanism of amplitude modulation.

Present methods do not provide instantaneous information to the auditory nerves. The mapping of spectral bands to electrodes inside the cochlea for these methods are based on tones experiments which cannot be produced by human vocal cords. Present speech strategy performance drops dramatically in noisy environments. Noise has many frequency components, and noise becomes the dominant factor in activating electrodes using the spectrum technique in a noisy environment. Also in the present speech strategy, the speech perceived by the cochlear implant users sounds like machine because the spectral is quantized and the spectral information are not continuously delivered to the electrodes. A new speech strategy is needed for cochlear implants that maps a temporal waveform to a spatial waveform to stimulate the auditory nerve and improves performance in all environments.

SUMMARY OF THE INVENTION

The present invention is directed to implementing a speech strategy based on the time duration between zero crossings of the speech to activate different electrodes inside the cochlea. The zero crossings contain both spectral and temporal speech information. The present invention enables this new speech strategy using the temporal information of speech to activate electrodes instead of the spectral information used by other speech strategies. The speech strategy of the present invention maps the temporal segment durations to spatial durations along the basilar membrane, and provides instantaneous, continuous information about the speech to electrodes aligned along the basilar membrane that activate the auditory nerve. The present invention uses the mechanical motion of the oval window to stimulate electrodes implanted inside the cochlea. The motion of the tympanic membrane, and the oval and round windows, follow the temporal waveform of the speech signal. Positive segments of the temporal waveform cause inward displacement of the oval membrane from its stationary position and negative segments causes outward retraction of the membrane. The zero-crossings in the temporal waveform indicate the time instants when the membranes in their stationary positions. In analogy to images, the zero-crossing is similar to an edge that shows contrast between inward (positive waveform) and outward (negative waveform) motion of the membrane.

Zero crossings carry instantaneous spectral information, where longer segment durations usually accompany low-frequency components of speech so they will activate electrodes near the apex of the cochlea and shorter segment durations usually accompany high-frequency components of speech so they will activate electrodes near the base of the cochlea. The amplitude of the waveform in each segment determines the amplitude of the electric current delivered to the corresponding electrode. Shorter segments will deliver a higher rate of pulses than longer segments since shorter segments associated with high frequencies. Pulse rate is another que to the brain about frequency. Implementing this strategy in the present invention provides instantaneous information of the frequencies and variations of the speech signal to the auditory nerves.

In one major aspect, the present invention provides a method that uses the length of the time duration of a segment between adjacent zero-crossing of the temporal waveform to determine which electrode to activate inside the cochlea, where a long time duration of a segment will activate an electrode located near the apex and a short time duration of a segment will activate an electrode located near the base.

In another aspect, the present invention provides a method that uses the maximum amplitude of the temporal waveform to determine the current amplitude.

In another aspect, the present invention provides a method that in which the pulse rate depends on the length of the time duration of the segment between zero-crossing where a shorter segment will deliver higher pulse rate and a longer segment will deliver a lower pulse rate.

In one major aspect, the present invention quantifies all possible segment time durations between adjacent zero-crossings to fixed number that range between 4 to 20 values and uses these lengths to determine which electrode is to be activated inside the cochlea to stimulate the auditory nerve.

In another aspect, the present invention provides cochlear implant users with more robust information about speech that the brain can interpret or learn as a new language.

In another aspect, the speech parameters used in the present invention are robust with respect to speech intelligibility in noisy environments. Noise has less impact on the zero crossing and segment durations.

In one major aspect, the present invention uses the temporal information of the speech to activate electrodes instead of the spectral information used by other speech strategies.

In another aspect, the present invention provides a processor that determines the time instant of the zero-crossing (the moment the wave changes from positive to negative), calculates the segment time duration (between successive zero-crossings), and quantifies the time duration to the nearest of the sixteen available durations (bins).

In another aspect, the present invention provides a processor that determines which electrode to stimulate, how much current to deliver to the electrode, and the current pulse rate to the electrode, where the location of the electrode is determined by the time duration of the segment.

In another aspect, the present invention, provides the auditory nerve with the instantaneous frequency by combining two adjacent time segments with the positive and negative waveforms and quantifies them to one period of sixteen predetermined periods, where the frequency of this period, calculated as 1/period, can be used to activate the electrode based on the place principle.

In another aspect, the speech signal may be passed through band-pass filters to separate the low-frequency components of the speech between 1000 and 3000 Hz and the high-frequency components between 3000 Hz and 7000 Hz, where the output signals of the band-pass filters are temporal waveforms from which their zero-crossings can be extracted and used to activate electrodes. This way fine temporal fluctuations that don't cause zero crossing in the original signal will be captured and mapped to electrodes.

In another aspect, the output of a low-band pass filter will activate electrodes near the apex of the cochlea and the zero-crossing of the temporal waveform coming from the high band-pass filter will activate electrodes near the base of the cochlea.

In another aspect, the hardware of the speech processor will be faster (real-time processing) and cheaper to build since it does not require intensive processing such as Fast Fourier Transform and filtering.

DETAIL DESCRIPTION

Figure 3:
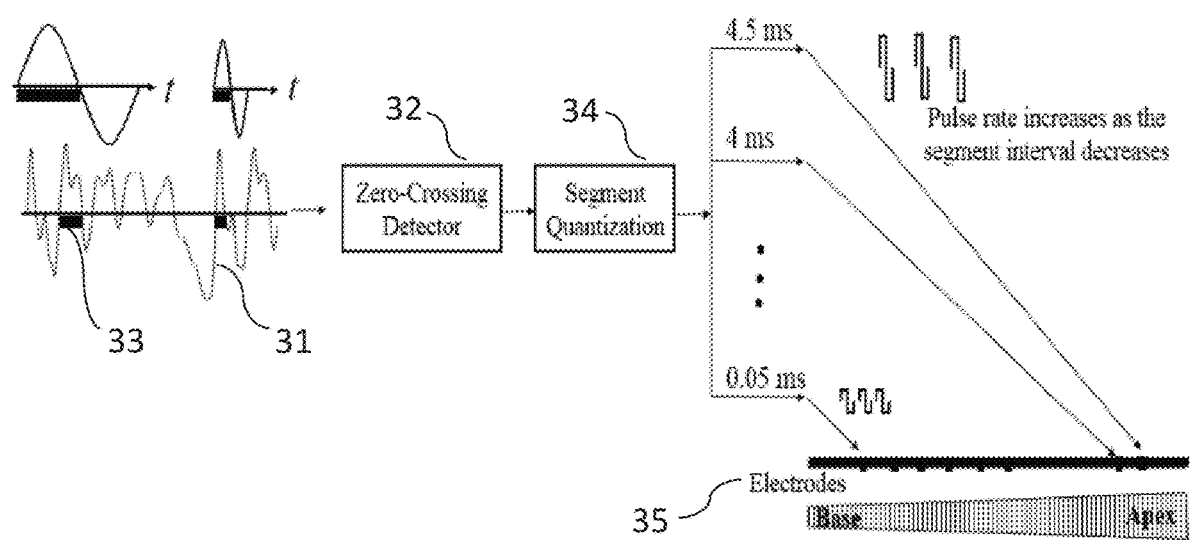
FIG. 3 is a non-limiting diagram that shows a method of the present invention to quantize time durations between zero-crossings to 4-20 fixed durations and map these durations to 4-20 electrodes.

In brief; referring to FIG. 3, a non-limiting diagram illustrates the method of the present invention quantizes the time durations between zero-crossings to 4-20 fixed durations and maps these durations to 4-20 electrodes. The amplitude of the waveform in a segment determines the amplitude of the current pulse. The pulse rate increases as the segment duration decreases. This strategy can be applied to hire number of electrodes if technology and surgical procedure succeeded in the insertion of higher number of electrodes in the cochlea.

Figure 4:
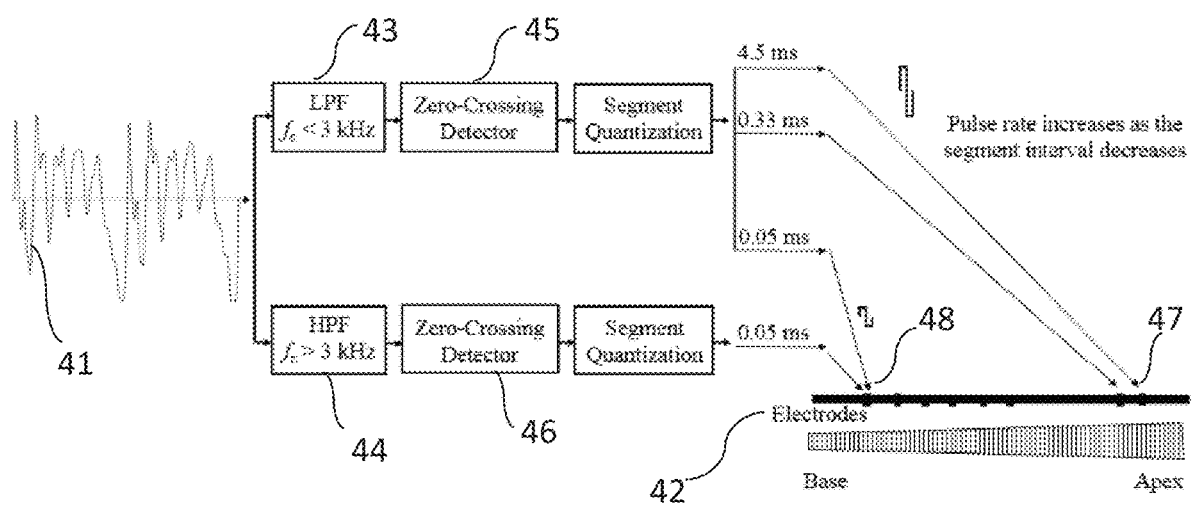
FIG. 4 is a non-limiting diagram that shows a method of the present invention to capture temporal fluctuations due to high-frequency components with low power that may not produce zero-crossings, the signal can be filtered to two different bands.

Referring to FIG. 4, a non-limiting diagram illustrates the method of the present invention captures temporal fluctuation resulting from high-frequency components with low power that may not produce zero-crossings; the signal can be filtered to two different bands. One band contains low- and mid-frequency spectral components, and the second band contains the high-frequency components. The segment durations between zero-crossings of the low band will activate electrodes near the apex of the cochlea. The segment durations between zero-crossing of the high band will activate electrodes near the base of the cochlea.

Figure 5:
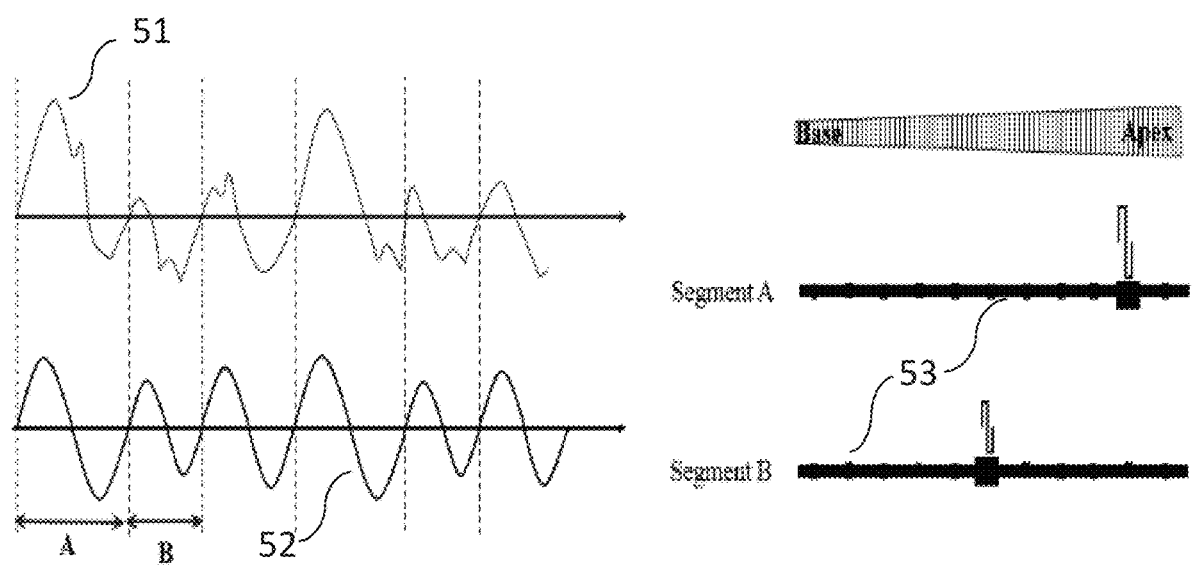
FIG. 5 is a non-limiting diagram that shows a method of the present invention to quantize the duration of two adjacent segments which involves three adjacent zero-crossings, and then represent the waveform in the two adjacent segments by a sinusoidal signal with period equal the sum of the quantized two-segment durations.

Referring to FIG. 5: a non-limiting diagram illustrates the present invention provides a method to quantize the duration of two adjacent segments which involves three adjacent zero-crossings, and then represents the waveform in the two adjacent segments by a sinusoidal signal with period equal to the quantized two-segment durations. Using this method, the speech intelligibility of the signal is quite high. The speech signal consists of a sequence of sinusoidal cycles. The frequency of each cycle can be considered as the instantaneous frequency of the speech waveform. This instantaneous frequency can be mapped to electrodes based on the tonotopic map of the basilar membrane. High-frequency components are mapped into electrodes near the base and low-frequency components are mapped into electrodes near the apex.

Figure 6:
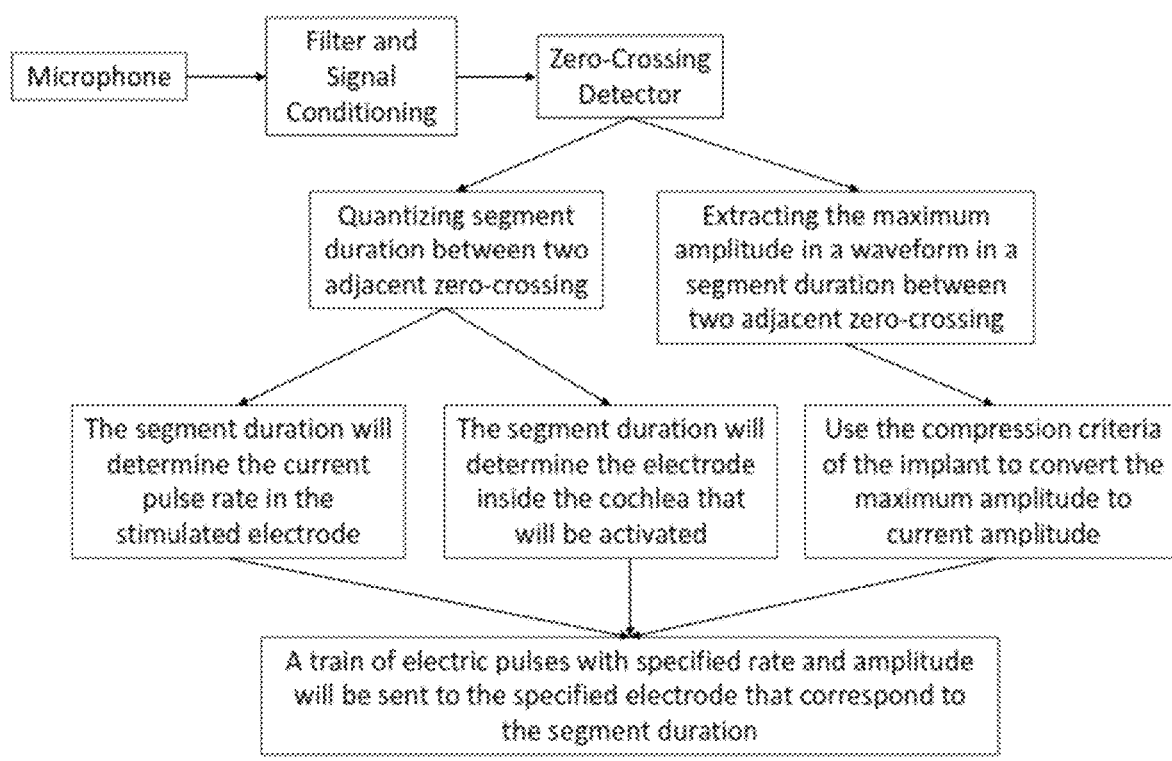
FIG. 6 is a non-limiting diagram that shows the method of the present invention as a functional flow diagram for processing speech based on the zero crossing behavior of the speech time waveform.

Referring to FIG. 6 a non-limiting functional flow diagram shows the steps in the method of the present invention for processing speech based on the zero crossing behavior of the speech time waveform. The steps include (1) detecting speech or sound (e.g., music) with a & microphone to convert to an electrical signal, (2) filtering and conditioning the signal to eliminate high and low frequency noise, base drift, and pre-emphasis of the signal, (3) detecting each zero-crossing of the signal and calculating the time durations between zero crossings, (4) quantizing segment durations, (5) extracting maximum amplitude in each segment, (6) determine current pulse rate, (7) determine electrode to activate, (8) convert maximum signal amplitude to current amplitude, (9) send electric pulses with specific rate and amplitude corresponding to segment duration.

In Detail: referring to FIG. 3, the method of the present invention quantizes the time durations between zero-crossings to 4-20 fixed durations and maps these durations to 4-20 electrodes. The amplitude of the waveform 31 in a segment determines the amplitude of the current pulse. The pulse rate increases as the segment duration interval decreases. The Zero-Crossing Detector (i.e., the speech processor) 32 quantizes segment duration 33 between two adjacent zero-crossings of the electrical signal and extracts the maximum amplitude in a waveform 31 in each segment duration between two adjacent zero-crossings. The length of the time duration of a segment 33 between adjacent zero-crossing of the temporal waveform 31 is used to determine which electrode 35 to activate inside the cochlea, where a long time duration of a segment will activate an electrode 35 located near the apex and a short time duration of a segment will activate an electrode 35 located near the base. The method of the present invention uses the maximum amplitude of the temporal waveform 31 to determine the current amplitude. The pulse rate of the current depends on the length of the time duration 33 of the segment between zero-crossing where a shorter segment will deliver higher pulse rate and a longer segment will deliver a lower pulse rate. The segment durations 33 between adjacent zero-crossings is quantized to the nearest segment duration of the 16 possible durations. The optimum 4 to 20 possible durations (bins) that will preserve the speech intelligibility are determined by statistical analysis and experiments on normal hearing subjects. The speech signals (HINT sentences and CNC Words) that was played during method testing to normal hearing subjects for evaluation were reconstructed from the 4 to 20 durations of quantized durations. The original waveform 31 in each segment is approximated by a sinusoidal wave with period equals to the nearest quantized segment duration 33 and the amplitude of the sinusoidal signal equals the maximum amplitude in the original waveform 31.

Referring to FIG. 4, the present invention provides a method and system for implementing a new speech strategy for cochlear implants that maps a temporal waveform 41 to a spatial waveform along the basilar membrane to stimulate the auditory nerve using intrachochlear electrodes 42. The present invention is directed to implementing said speech strategy based on the zero crossing behavior of the speech time waveform 41, where the zero crossing contains both spectral and temporal speech information. The present invention uses the temporal information of the speech to activate electrodes 42 instead of the spectral information used by other speech strategies. The speech strategy implemented in the present invention maps the temporal segment durations [FIG. 3, 33] to spatial durations, enabling instantaneous, continuous information about the speech to electrodes 42 that stimulate the auditory nerve. In preferred embodiments, the speech signal 41 can be passed through band-pass filters 43 and 44 to separate the low-frequency components of the speech between 100 and 3000 Hz and the high-frequency components between 3000 Hz and 7000 Hz. The outputs of these two band-pass filters 43 and 44 are temporal waveforms from which their zero-crossings are extracted and used to activate electrodes 42. The Zero-Crossing Detectors (i.e., the speech processor) 45 and 46 quantize segment duration [FIG. 3, 33] between two adjacent zero-crossings of the electrical signal from the band-pass filters 43 and 44 respectively and extracts the maximum amplitude in a waveform 41 in each segment duration between two adjacent zero-crossings. The output of the low-band pass filter 43 generally activates electrodes 47 near the apex of the cochlea, and the zero-crossing of the temporal waveform coming from the high band-pass filter 44 generally activates electrodes 48 near the base of the cochlea. Where the quantized segment duration time output from the bandpass filters 43 and 44 is approximately the same (e.g., 0.05 ms) electrodes 48 near the base of the cochlea are generally activated. The amplitude of the waveform 41 in a segment determines the amplitude of the current pulse. The pulse rate increases as the segment duration interval decreases.

Referring to FIG. 5, the input to a Zero-Crossing Detector (i.e., the speech processor) [FIG. 3, 32] of the present invention is the speech waveform 51 picked up by a microphone (not shown). The Zero-Crossing Detector (i.e., the speech processor) [FIG. 3, 32] filters out frequencies below 100 Hz and frequencies above 8000 Hz. The Zero-Crossing Detector (i.e., the speech processor) [FIG. 3, 32] removes any dc offset (base drift in the acoustic wave) and determines the time instant of the zero-crossing (the moment the wave changes from positive to negative) and produces a smoother waveform 53. The Zero-Crossing Detector (i.e., the speech processor) [FIG. 3, 32] calculates the segment time duration A and B (between successive zero-crossings) [FIG. 3, 33]

and quantizes the time duration to the nearest of the sixteen available durations (bins). The sixteen durations have been specified by statistical analysis to minimize the quantization error and minimize the deterioration of the speech intelligibility due to quantization. These duration bins have been specified to be [0.05 0.1 0.15 0.2 0.3 0.4 0.5 0.7 1.0 1.5 2.0 2.5 3.0 3.5 4.0 4.5] milliseconds. Same method has been used to derive the 8 and 4 duration bins for the 8 and 4 electrodes. The bins for the 8 electrodes is [0.1 0.3 0.5 0.7 1 1.6 2.2 3] milliseconds, and the bins for the 4 electrodes is [0.1 0.5 1.0 2.5] milliseconds. Same method can be used to derive the durations bins for any number of electrodes that are implanted in the cochlear implant user.

After quantizing the segment duration, A and B, the amplitude of the waveform on that segment is saved in a storage device (not shown). For each segment, A and B, the Zero-Crossing Detector (i.e., the speech processor) [FIG. 3, 32] determines which electrode 52 to stimulate, how much current to deliver to the electrode 53, and the current pulse rate to the electrode 52. The location of the electrode 53 is determined by the time duration of the segment. Longer segments such as A will activate electrodes further away from the base and closer to the apex of the cochlea. Shorter segments such as B will activate electrodes closer to the base of the cochlea. This technique basically maps the time durations, A and B, to spatial distances along the basilar membrane. The amplitude of the waveform 51 determines the amount of current delivered to the electrode 53. The range of the current may be determined by an audiologist for each electrode 53. The rate of pulse delivered is determined by the segment duration, A or B. Longer segments deliver lower pulse rates. This is another cue to the brain about the pitch information for each frequency component.

The Zero-Crossing Detector (i.e., the speech processor) [FIG. 3, 32] of the present invention may combine at least two adjacent time segments with the positive and negative waveforms and quantize them to one period of sixteen predetermined periods. Two adjacent segments of zero crossings is similar to a segment between two zero crossings that happened when the waveform 52 changes from a negative to positive waveform. The zero crossing when the waveform 52 changes from positive to negative is ignored. The frequency of this period, calculated as 1/period, can be used to activate the electrode 53 based on the place principle. This will provide the auditory nerve with the instantaneous frequency of the speech. While the zero-crossing technique will miss small fluctuations with high vibration rates due to high-frequency components, the speech signal 51 can be passed through band-pass filters [FIG. 4, 43 and 44] to separate the low-frequency components of the speech between 100 and 3000 Hz and the high-frequency components between 3000 Hz and 7000 Hz. The outputs of these two band-pass filters [FIG. 4, 43 and 44] are temporal waveforms from which their zero-crossings will be extracted as before and used to activate electrodes. The output of the low-band pass filter [FIG. 4, 43] will activate electrodes near the apex of the cochlea, and the zero-crossing of the temporal waveform coming from the high band-pass filter filters [FIG. 4, 44] will activate electrodes near the base of the cochlea.

Figure 1:
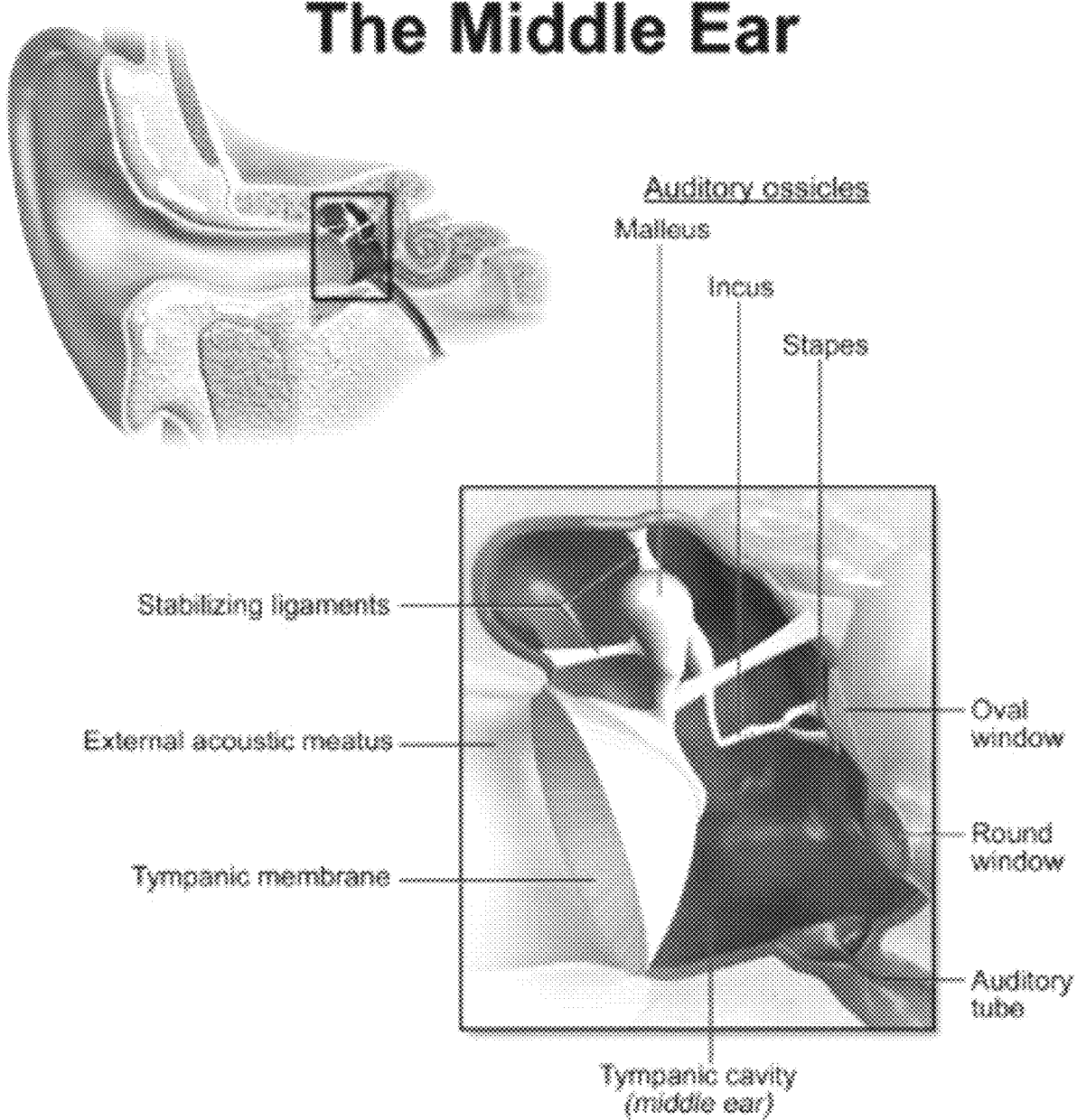
FIG. 1 shows a diagram of the auditory system in a human.
Figure 2:
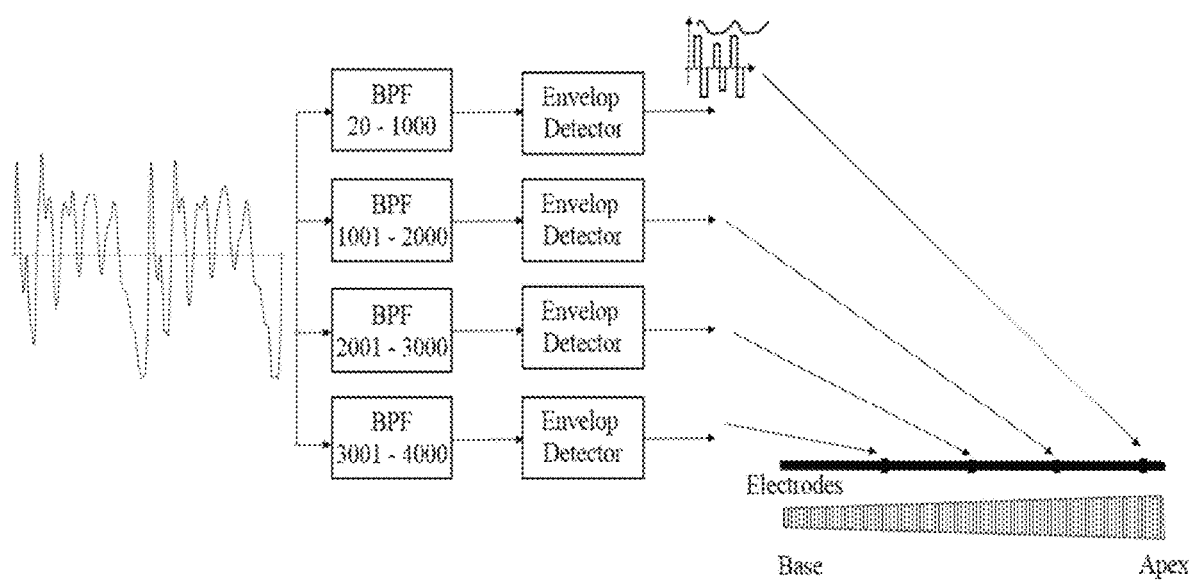
FIG. 2 illustrates a typical method of implementing contemporary speech strategies.

The present invention implements a speech strategy that requires simpler circuitry compared to contemporary methods [FIG. 2] and will be lower cost to manufacture, smaller in size, and provide real-time processing. The method of the present invention does not require a digital signal processor to calculate the fast Fourier transform. It does not require 16 band-pass filters with 16 low-pass filters to extract the envelopes of the waveforms typical of contemporary systems. In contrast, the present invention in a preferred embodiment requires only a Zero-crossing Detector with a timer (i.e., speech processor) [FIG. 3, 32; FIG. 4, 45 and 46] to implement a speech strategy based on the zero crossing behavior of the speech time waveform, where the zero crossing contains both spectral and temporal speech information.

Referring to FIG. 6, in a preferred embodiment, the Zero-Crossing Detector [FIG. 3, 32; FIG. 4, 45 and 46] implements the method of the present invention including the steps of (1) detecting speech or sound (e.g., music) with a microphone to convert to an electrical signal, (2) filtering and conditioning the signal to eliminate high and low frequency noise, base drift, and pre-emphasis of the signal, (3) detecting each zero-crossing of the signal and calculating the time durations between zero crossings, (4) quantizing segment durations, (5) extracting maximum amplitude, (6) determine current pulse rate, (7) determine electrode to stimulate, (8) convert maximum signal amplitude to current amplitude, (9) send electric pulses to electrodes corresponding to segment duration.

The method and system provided by the present invention has been subjected to preliminary testing. Speech performance of the present invention (ZCP) was evaluated on two cochlear implant users. The present invention was compared against the default commercial strategy FS4 available from MED-EL Corporation. The result is shown in Table 1.

TABLE 1

| | | FS4 | ZCP |
|---|---|---|---|
| Information transmission analysis of VCVs (%) | VCV (% correct, 10 reps) | 61.9 | 67.5 |
| | Duration | 94.3 | 79 |
| | Envelope | 80.7 | 96.2 |
| | Frication | 43.5 | 96.7 |
| | Nasality | 90.1 | 88.9 |
| | Place | 66.7 | 54.2 |
| | Voicing | 66.7 | 91.1 |
| | Monosyllabic words (% correct, 40 words) | 70 | 62.5 |
| | Monosyllabic words by phoneme (% correct, 40 words) | 88.3 | 83.3 |

When listening to music, cymbals and bass are very clear and relatively natural in comparison to the FS4 strategy. Given that this is acute testing with no real attempt to optimize the ZCP strategy for CI users, and train subjects to the new strategy, the present invention exceed expectation. Usually it takes months for cochlear implant users to get used to a new speech strategy, just like learning a new accent for normal hearing subjects.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

The invention claimed is:

1. A process providing a method to stimulate an auditory nerve using cochlear implant electrodes, comprising:

providing a speech processor that governs which electrode to activate in a plurality of electrodes in response to an audio signal, how much current to deliver to each of said electrodes, and pulse rate of said current;

separating said audio signal into low frequency components in a range of 100 Hz to 3000 Hz and high frequency components in a range of 3000 Hz to 7000 Hz to produce speech time waveforms;

determining zero crossing of said speech time waveforms, the zero-crossing containing both spectral and temporal speech information;

quantizing the time durations between zero-crossings to 4 to 20 fixed durations and mapping these durations to 4 to 20 electrodes;

using said temporal speech information to activate said electrodes, mapping temporal segment durations to spatial durations along a basilar membrane to provide electric pulsed signals to said electrodes to stimulate said auditory nerve, and determining time duration of a temporal segment between adjacent zero-crossing of a speech time waveform to determine which electrode to activate inside a human cochlea, said electrodes positioned between apex and base of said cochlea, wherein all possible segment time durations between adjacent zero-crossings are quantified to a fixed number in a range between 4 to 20 values, and a length of time duration determines which electrode in said 4 to 20 electrodes to activate, and wherein a long time duration of a segment activates an electrode located near said apex and a short time duration of a segment activates an electrode located near said base.

2. A system to stimulate an auditory nerve using cochlear implant electrodes, said system performing the process of claim 1, wherein all possible segment time durations between adjacent zero-crossings quantified to a fixed number in the range between 4 to 20 values are used to determine which electrode is to be activated applying an electrical current to stimulate the auditory nerve.

3. The system of claim 2, further comprising a speech processor, wherein the speech processor quantizes segment time duration between two adjacent zero-crossings and extracts a maximum amplitude in a speech time waveform in each segment duration, and wherein an amplitude of said current delivered to said electrodes directly correlates with signal strength in the corresponding segment time duration between zero-crossing of the audio signal.

4. The system of claim 2, wherein signal pulse rate will increase as said segment time duration between zero-crossing decreases.

* * * * *